US00PP36814P2

(12) United States Plant Patent
Hansen

(10) Patent No.: US PP36,814 P2
(45) Date of Patent: Jul. 8, 2025

(54) ***AGASTACHE* PLANT NAMED 'Pinky Pie'**

(50) Latin Name: ***Agastache* hybrid**
Varietal Denomination: Pinky Pie

(71) Applicant: Hans A. Hansen, Zeeland, MI (US)

(72) Inventor: Hans A. Hansen, Zeeland, MI (US)

(73) Assignee: Walters Gardens. Inc., Zeeland, MI (US)

( * ) Notice: Subject to any disclaimer, the term of this patent is extended or adjusted under 35 U.S.C. 154(b) by 0 days.

(21) Appl. No.: 18/831,467

(22) Filed: Jan. 29, 2025

(51) Int. Cl.
*A01H 5/02* (2018.01)
*A01H 6/50* (2018.01)

(52) U.S. Cl.
USPC ..... Plt./399
CPC ..... *A01H 6/50* (2018.05); *A01H 5/02* (2013.01)

(58) Field of Classification Search
USPC ..... Plt./263.1, 399
See application file for complete search history.

*Primary Examiner* — Karen M Redden

(57) ABSTRACT

A new and unique cultivar of hyssop, *Agastache* plant named 'Pinky Pie' with medium-sized, dense, full, rounded, well-branched, winter-hardy habit. The large, lavender-pink colored flowers emerge from apricot-colored buds and cover the top two-thirds of the plant, with mauve-pink calyxes in densely branched panicles over an extended period beginning in early summer and continuing into fall.

1 Drawing Sheet

Botanical denomination: *Agastache* hybrid.
Variety designation: 'Pinky Pie'.

STATEMENT REGARDING PRIOR DISCLOSURES UNDER 37 CFR 1.77(b)(6)

The first offer for sale of *Agastache* 'Pinky Pie' was made by Walters Gardens, Inc. on Feb. 1, 2024. Walters Gardens, Inc. obtained the new plant and information about the new plant directly from the inventor. No plants of *Agastache* 'Pinky Pie' have been sold or offered for sale in this country or anywhere in the world nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct Anise Hyssop plant or Hummingbird Mint from the genus *Agastache* and given the cultivar name 'Pinky Pie'. The new plant was the result of a single seedling selection from a cross on Jul. 20, 2019, by the inventor between the proprietary, unreleased, hybrid, 'Coral King' (not patented) as the female or seed parent and the proprietary, unreleased, proprietary hybrid 17-9-2 (not patented) as the male or pollen parent. The seeds from the pollination were collected in the autumn of 2019. The single individually selected seedling was eventually given the breeder code 19-7-2 after being first isolated from trials at a nursery in Zeeland, MI during the summer of 2021. It was selected for the final introduction in the summer of 2022.

*Agastache* 'Pinky Pie' has been asexually propagated at the same nursery in Zeeland, MI originally by basal shoot cuttings in 2021, followed by traditional shoot tip and stem cutting procedures and found to reproduce plants that are identical and exhibit all the characteristics of the original plant in successive generations of asexual propagation.

The new plant, *Agastache* 'Pinky Pie', has not been observed under all possible environments. The phenotype may vary slightly with different environmental conditions, such as temperature, light, fertility, moisture and maturity levels, but without any change in the genotype.

In comparison to the new plant, the seed parent has a taller habit and the flowers are a deeper reddish coral and the calyces are a deeper wine color. The male parent has a taller more upright habit and the flower was darker coral-colored.

The nearest comparison varieties known to the inventor are: 'Apricot Sprite' (not patented), 'Guava Lava' U.S. Plant Pat. No. 36,001, 'Kudos Coral' U.S. Plant Pat. No. 25,613, 'Kudos Mandarin' U.S. Plant Pat. No. 25,381, 'Mango Tango' U.S. Plant Pat. No. 28,747, 'Peachie Keen' U.S. Plant Pat. No. 25,886, 'Queen Nectarine' U.S. Plant Pat. No. 34,896, and 'Summer Sunset' U.S. Plant Pat. No. 23,623.

'Apricot Sprite' has a slightly smaller habit with flowers of orangish-apricot color. 'Guava Lava' has a slightly larger habit with flowers that are coral-orangish coloration on densely branched panicles. 'Kudos Mandarin' has deeper orange-colored flowers with a significantly smaller habit. 'Kudos Coral' has a narrower and smaller habit in both height and width, and the flower color is more reddish-colored. 'Mango Tango' has a shorter and more compact habit and the flowers are light peach to mango-orange colored. 'Peachie Keen' has a slightly smaller habit with apricot-peach-colored flowers and purplish-pink calyxes. 'Queen Nectarine' is significantly taller and broader in habit, and the flowers are a light peach color. 'Summer Sunset' is less winter-hardy, has a smaller and narrower habit, and the flower color are more orangish-colored. Both 'Kudos Mandarin' and 'Kudos Coral' have not overwintered under similar conditions where the new plant has survived the winter.

*Agastache* 'Pinky Pie' is distinct from the parents and all other anise hyssop known to the inventor in the following combined traits:

1. Medium-sized, dense, well-branched, full, rounded, winter-hardy habit;
2. Large flowers of lavender-pink coloration in densely branched panicles;
3. Long bloom time starting with apricot-colored buds and the effectiveness is extended by persistent, mauve-pink-colored calyxes after the calyces drop;
4. Foliage is medium green;
5. Flowers covering the upper two-thirds of the plant beginning in early summer and continuing to fall.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
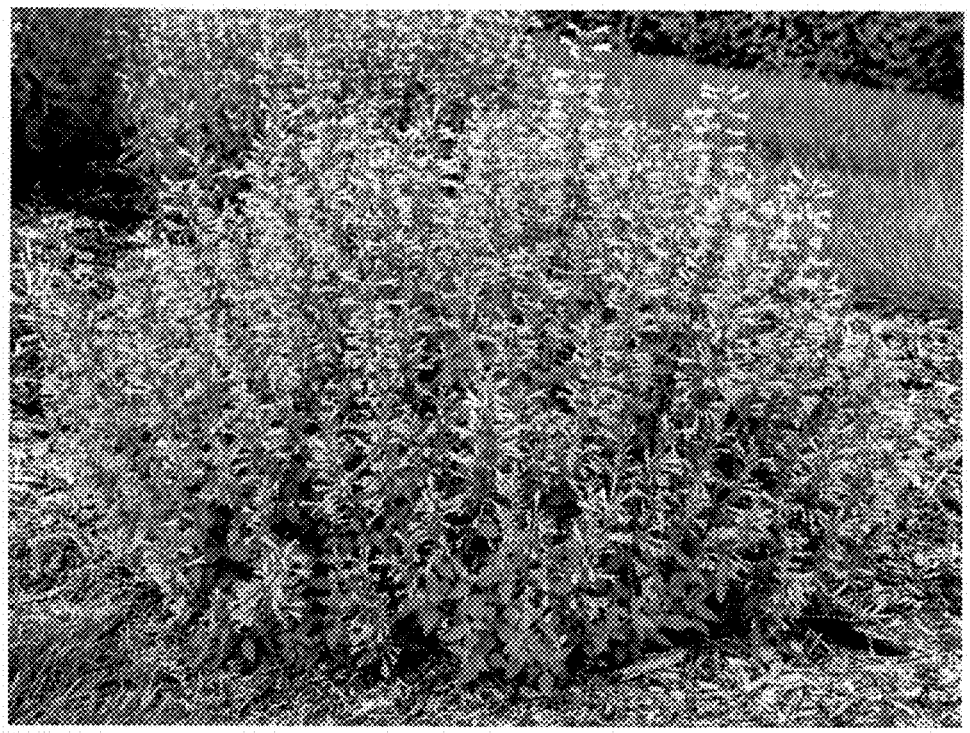
FIG. 1 shows a landscape view of a two-year-old plant in mid-season flower in an overwintered trial block at a nursery near Zeeland, Michigan.
Figure 2:
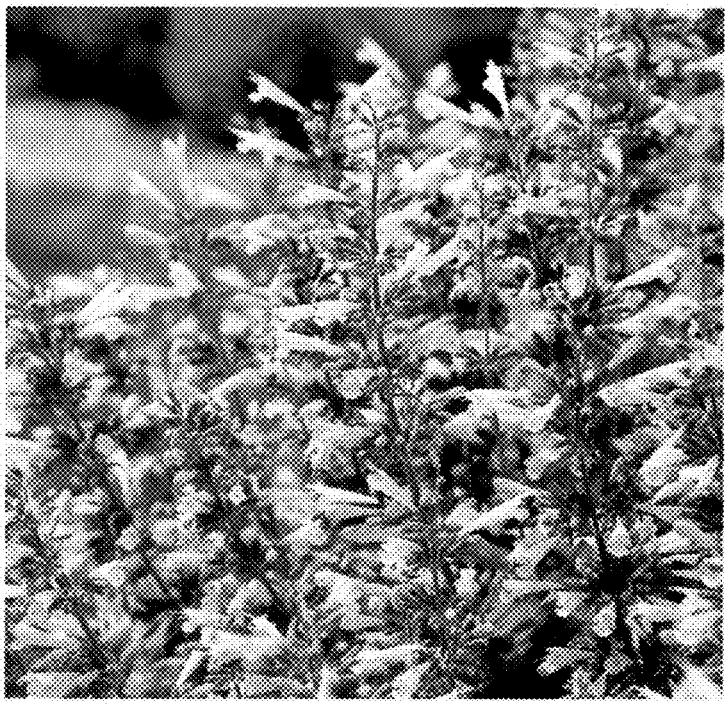
FIG. 2 shows a close-up of the scapes with flowers, buds, and calyxes.

The following is a detailed description of the new *Agastache* cultivar 'Pinky Pie' based on observations of a three-year-old specimen grown with supplemental watering and fertilizer as needed in a display garden at a wholesale perennial nursery in Zeeland, MI. Color descriptions are from the 2015 edition of The Royal Horticultural Society Colour Chart except where common dictionary terms are used.

Parentage: The female or seed parent is the unreleased, non-patented, proprietary *Agastache* known by 'Coral King' (not patented), the male or pollen parent is the unreleased, non-patented, proprietary *Agastache* known by the breeder code 17-9-2 (not patented);

Propagation—method: Basal shoot cuttings;

*Time to initiate roots*.—About 10 days.

*Crop time*.—Finishing in a 3.8-liter pot from a 25 mm plug in 10 to 12 weeks.

Plant habit: Multi-stemmed herbaceous perennial, rounded, heavily branched;

Plant size: Without growth retardants or pinching—to about 42 cm tall and 66 cm across;

Roots: Fibrous, well-branched; to about 2 mm diameter near the base; color light tan nearest RHS 165D depending on soil type;

Stem: Quadrangular; stiff; wiry; micro-puberulent to micro-glandular; to about 3 mm across at the base and 42 cm tall with flowering starting about 21 cm above the soil; three nodes below branched peduncle; internodes average about 5.6 cm long; to about twenty stems per plant;

Primary branches: Quadrangular; opposite; to about two per stem; to about 22 cm long and about 2 mm diameter at base;

Secondary branches: Quadrangular; opposite; about four per primary branch; to about 6 cm long and 1 mm diameter at base;

Primary and secondary branch color: Proximal portions between RHS 146C and RHS 147C, distal portions nearest RHS 138A; nodes nearest RHS 146B;

Leaf: Simple; opposite; lanceolate; base rounded to nearly truncate; apex narrowly acute; margin irregularly serrate to entire; adaxial glabrous and matte, abaxial micro-glandular and matte;

Leaf size: To about 51 mm long and 27 mm across near base, decreasing distally; average about 32 mm long and 16 mm across;

Leaf color: Young expanding adaxial nearest RHS 137A, abaxial between RHS 147C and 191A; mature adaxial between RHS 137A and RHS NN137C, abaxial between RHS 147B and RHS 147C;

Leaf venation: Reticulate; glabrous and slightly impressed adaxial, micro-glandular and costate abaxial;

Vein color: Adaxial nearest RHS 137A, abaxial midrib and primary veins between RHS 146D and RHS 147C, secondary veins nearest RHS 137C;

Leaf fragrance: Moderately herbal, minty;

Petiole: Glabrous adaxial and micro-puberulent to micro-glandular abaxial; concavo-convex; to 17 mm long and 2 mm across, average 5 mm long and 1.5 mm;

Petiole color: Adaxial nearest RHS 138A; abaxial nearest RHS 146D in longitudinal center and edges nearest RHS 138A;

Inflorescence: In densely branched panicle with about 2 compound branches or short whorls in axils; 12 to 60 flowers on two branchlets per node; up to 12 nodes per central stem, and 6 cm across; total inflorescence flowering portion about 21 cm long and about 16 cm across; each stem flowering for about 5 weeks but remain effective for about 6 weeks or more because of the strongly pigmented persistent calyxes; repeating if deadheaded;

Bloom period: Early summer through frost in Zeeland, Michigan;

Peduncle: Average about 42 cm tall and about 3 mm at base; micro-puberulent to micro-glabrous; branched; attitude upward;

Peduncle color: Proximally between RHS 146C and RHS 147C, distally nearest RHS 138A;

Flower: Perfect; complete; zygomorphic; sympetalous; bilabiate, with five united petals forming an upper labium 2-lobed and lower labium 3-lobed initially concaved becoming flat with maturity; attitude outwardly to slightly upwardly;

Flower size: To about 31 mm long to exerted stamen, about 9 mm tall and 5.5 mm across; corolla to about 26 mm long, 8 mm tall, 5.5 mm across, 4 mm diameter at fusion of two labium, and 1 mm diameter at base;

Flower lasting: Individual flowers open for about 3 days; individual panicle lasting for about 5 weeks;

Bud on day prior to opening: Arcuate, clavate to obelliptical; to about 25 mm long, 4 mm tall, and 3.7 mm wide just before the apex and 2 mm wide at base;

Bud color: Petals nearest RHS 25C at apex, proximal portion nearest RHS 173C; calyx ventral portion nearest RHS 147C, dorsal portion and veins moderately blushed between RHS N79A and RHS N79B;

Petals: Both upper and lower labium glabrous adaxial, micro-puberulent to micro-glandular abaxial; matte both adaxial and abaxial; both labia proximally fused forming tube in the basal 23 mm;

Upper labium: 2-lobed, about 26 mm long and 4 mm across toward apex; lobes centrally cleft about 1.5 mm deep and 2 mm across at base; lobe apices rounded; margin entire;

Lower labium: 3-lobed; about 26 mm long, 3 mm wide at fusion and 5 mm across near apex; reflexed downward in distal 4 mm with flower maturity; middle lobe concavo-convex, about 4 mm long and 4 mm across, with a rounded emarginate apex 1 mm deep, and crenate margin; two side lobes of lower petal reflexed, about 3 mm long and 3 mm wide, with rounded apex and entire margin;

Petal color: Abaxial and adaxial upper labium nearest RHS N75D, lower labium adaxial nearest RHS N75B, lower labium abaxial nearest RHS N75C; corolla tube adaxial and abaxial dorsal and ventral portion nearest RHS N75D;

Calyx: Tubular; to about 8 mm long and diameter about 3 mm;

Sepals: Five; linear; acute apices; entire margin; fused into tube in basal 6 mm, free in the distal 2 mm; glabrous adaxial and micro-glandular to micro-puberulent abaxial; to about 8 mm long, and 2 mm across at fusion;

Calyx color: Adaxial nearest RHS 146C with margins moderately blushed nearest RHS N79A, abaxial ventral portion nearest RHS 147C, dorsal portion and veins moderately blushed between RHS N79A and RHS N79B;

Gynoecium: Single; to 31 mm long; exerted;

*Style*.—One, about 29 mm long and about 0.3 mm diameter; terete; glabrous; straight; color nearest RHS N81B upon first opening in the distal 2 to 3 mm and extending proximally to the distal 7 to 8 mm before dehiscence, proximally nearest RHS NN155C.

*Stigma*.—Bifid and reflex; each segment about 1 mm long and about 0.3 mm diameter; tapering to a pointed apex; color nearest RHS N81C upon opening and developing to nearest RHS nearest RHS N81B at dehiscence.

*Ovary*.—Elliptical with rounded apex and rounded base; 1 mm long and 0.7 mm diameter; color between RHS 146D and RHS 145A.

Androecium:

*Stamen*.—In two sets of two, exerted, adnate to the inner corolla.

*Filaments*.—Two longer and two shorter; paired and exerted; longer pair adnate in the basal 16 mm and free in the proximal 9 mm; shorter pair adnate in the basal 14 mm and free in the proximal 8 mm; color between RHS N80C and RHS N81D.

*Anthers*.—Dorsifixed; versatile; folded; longitudinal; about 1.2 mm long and about 0.8 mm across; color nearest RHS 77A.

*Pollen*.—Abundant; color nearest RHS 11D.

Fragrance: None detected;

Pedicel: Cylindrical; puberulent; aspect outwardly; to about 2 mm long and 0.7 mm diameter; color nearest RHS N186C;

Fruit: Two carpels;

Seed: Nutlet, typically one to two per naturally pollinated flower, ellipsoidal; about 1 mm long, 0.8 mm across and 0.5 mm thick;

Seed color: Nearest 202A;

Resistance: 'Pinkie Pie' is resistant to *Odocoileus hemionus* browsing but has not been tested or shown resistance to other pests and diseases common to *Agastache*.

Hardiness: The new plant has survived USDA winter hardiness zones 5 to 9 but has not been tested yet beyond these temperatures.

It is claimed:

1. A new and distinct cultivar of *Agastache* plant named 'Pinky Pie' as herein described and photographed.

* * * * *